United States Patent [19]

van Zon

[11] 4,254,034
[45] Mar. 3, 1981

[54] MACROCYCLIC POLYETHER COMPLEXES AND METHOD FOR POLYETHER ISOLATION USING SAID COMPLEXES

[75] Inventor: Arie van Zon, Amsterdam, Netherlands

[73] Assignee: Shell Oil Company, Houston, Tex.

[21] Appl. No.: 88,201

[22] Filed: Oct. 23, 1979

[30] Foreign Application Priority Data

Nov. 10, 1978 [GB] United Kingdom ............... 43945/78

[51] Int. Cl.³ .......................................... C07D 323/00
[52] U.S. Cl. .................................................... 260/338
[58] Field of Search ........................................ 260/338

[56] References Cited

U.S. PATENT DOCUMENTS

| 3,562,295 | 2/1971 | Pedersen | 260/338 |
| 3,687,978 | 8/1972 | Pedersen | 260/340.3 |
| 3,928,386 | 12/1975 | Dale et al. | 260/338 |
| 3,965,116 | 6/1976 | Cram | 260/338 |
| 3,997,562 | 12/1976 | Liotta | 260/338 |

OTHER PUBLICATIONS

Chemical Abstracts, vol. 82, (1975), 124273d.
J. M. Timko et al., Jour. Am. Chem. Soc., vol. 99, No. 13, Jun. 22, 1977, pp. 4207–4219.

*Primary Examiner*—Norma S. Milestone

[57] ABSTRACT

A novel complex of 1,4,7,10,13,16-hexaoxacyclooctadecane (18-crown-6) and dimethylcarbonate or dimethyloxalate, containing one molecule of dimethylcarbonate or dimethyloxalate for each molecule of 18-crown-6, is useful in isolating 18-crown-6 from mixtures containing it. In the isolation or purification process described, 18-crown-6 is isolated from a mixture containing it by reacting the 18-crown-6 with dimethylcarbonate or dimethyloxalate to form a complex substantially in the form of a dispersed solid in a solution containing the non-complexed material of the mixture, separating the dispersed complex from the solution and disassociating the dimethylcarbonate or dimethyloxalate from the separated complex.

13 Claims, No Drawings

MACROCYCLIC POLYETHER COMPLEXES AND METHOD FOR POLYETHER ISOLATION USING SAID COMPLEXES

BACKGROUND OF THE INVENTION

This invention relates to novel complexes of the macrocyclic polyether, 1,4,7,10,13,16-hexaoxacyclooctadecane, and to a process for the isolation of 1,4,7,10,13,16-hexaoxacyclooctadecane from mixtures containing this polyether in which the novel complexes are advantageously employed to effect separation of the polyether from the mixture.

Macrocyclic polyethers such as 1,4,7,10,13,16-hexaoxacyclooctadecane have demonstrated ability to solubilize or complex metal cations in both polar and relatively non-polar media, which, in turn, makes them valuable reagents in a variety of synthesis and separation processes. In this regard, 1,4,7,10,13,16-hexaoxacyclooctadecane, which is also known by its trivial name "18-crown-6," has special utility in the complexing of lower alkali metal cations e.g. potassium, in such diverse media. The disclosure of metal cation complexing properties for 18-crown-6 has stimulated considerable technical interest and, as a result, a number of synthetic techniques have been proposed for preparing the macrocyclic polyether. These preparative processes for 18-crown-6 include:

(1) Catalytic oligomerization of ethylene oxide, see U.S. Pat. No. 3,928,386.
(2) Reaction of tetraethylene glycol with bis(2-chloroethyl) ether in the presence of potassium hydroxide and tetrahydrofuran without addition of water, as described in "Synthesis" 1976, 515–516.

While the aforementioned preparative techniques for 18-crown-6 show a considerable variation in product yield and cost of starting materials, all share the same disadvantage from a practical or commercial standpoint in that difficult and/or commercially unattractive procedures are required to isolate the 18-crown-6 from the reaction mixture.

The technique disclosed for isolating 18-crown-6 from the reaction mixture obtained by process (1) above involves chromatographic separation on acid-washed alumina or silica and elution with readily volatile hydrocarbons. This isolation procedure is not particularly attractive from a commercial standpoint because the adsorption capacities of alumina or silica for the 18-crown-6 are rather low and the used alumina or silica must be regenerated or discarded and replaced by fresh alumina or silica.

In the reference process (2) above, potassium chloride and tetrahydrofuran are removed from the reaction mixture and the resulting product is distilled to afford a crude 18-crown-6 overhead product. Subsequently the distilled 18-crown-6 is mixed with acetonitrile and the mixture obtained is cooled to a very low temperature, e.g., −45° C., to precipitate the 18-crown-6-acetonitrile complex which forms on addition of the acetonitrile. The precipitated complex is then filtered off and the acetonitrile is evaporated from the filtered complex at sub-atmospheric pressure with gentle heating. The residue is then distilled to obtain the 18-crown-6 as a distillate. One disadvantage of using acetonitrile in accordance with reference process (2) for isolation of the 18-crown-6 is high solubility of 18-crown-6-acetonitrile complex in acetonitrile at ambient temperatures. Because of this high solubility, very low temperatures must be used to precipitate the complex from the excess acetonitrile and even then the complexed 18-crown-6 is obtained in rather low yield. A further disadvantage of reference process (2) above is that it includes at least one step wherein the 18-crown-6 is distilled overhead, and therefore, additional measures must be taken to avoid the occurrence of powerful and destructive explosions which are known to occur during the distillation of 18-crown-6, see "Chemical and Engineering News," Sept. 6, 1976, page 5 and Dec. 13, 1976, page 5.

The isolation of 18-crown-6 from reaction mixtures can also be carried out using nitromethane as the complexing agent, as described and claimed in co-pending application, Ser. No. 38,039, filed May 11, 1979, Common Assignee. The isolation can be carried out at ambient or somewhat lower temperature (because of the lower solubility of the 18-crown-6-nitromethane complex in nitromethane). The 18-crown-6 need not to be distilled in order to separate it from the 18-crown-6-nitromethane complex as nitromethane can be removed from the complex by heating the complex at sub-atmospheric pressure. However, the use of nitromethane implies some drawbacks, expecially in large scale operations, due to its toxicity and explosion danger when subjected to higher temperatures. Furthermore, the complex contains two molecules of nitromethane per molecule of 18-crown-6, so that two moles of the complexing agent must be removed from each mole of the separated 18-crown-6-nitromethane complex obtained.

From the foregoing, it is apparent that considerable advantage would be obtained if a simple and cost effective means could be found for isolating 18-crown-6 from reaction mixtures which avoids the commercial impracticalities and potential hazards associated with previous separation techniques.

Various complexes between 18-crown-6 and other compounds have been prepared and are disclosed, for example, in U.S. Pat. Nos. 3,562,295, 3,687,978 and 3,997,562 and in Chem. Abst., Vol. 82, No. 124273d. Complexes of 18-crown-6 and dimethyl acetylenedicarboxylate are disclosed in:

Goldberg, Acta Cryst., Sect. B, 31, 754 (1975)
Timko et al., JACS, 99, 4207 (1977)
British Patent Specification 1,481,671 Neither the use of such complexes to isolate 18-crown-6 from reaction mixtures or the presence of complexes of 18-crown-6 and dimethylcarbonate or dimethyloxalate are disclosed by these references.

SUMMARY OF THE INVENTION

It has now been found that 1,4,7,10,13,16-hexaoxacyclooctadecane or 18-crown-6 will react with dimethylcarbonate or dimethyloxalate to form novel complexes which can be advantageously employed to isolate the 18-crown-6 from mixtures containing it, including mixtures obtained as reaction products in the aforementioned synthesis processes. These novel complexes of 18-crown-6 and dimethylcarbonate or dimethyloxalate especially attractive in that they exhibit lower solubility in the complexing medium than complexes previously employed to separate 18-crown-6 (18-crown-6-acetonitrile complex) thus allowing the 18-crown-6 to be separated in very high yield in a process scheme similar to that previously used without the need for cooling to very low temperatures to precipitate the complex. A further advantage of the present invention is that the complex between 18-crown-6 and dimethylcarbonate or dimethyloxalate forms selectively in the presence of one or more other macrocyclic polyethers such as 1,4,7,10,13-pentaoxacyclopentadecane (15-crown-5). The use of dimethylcarbonate or dimethyloxalate as the complexing agent also aids in reducing the risks of toxicity and explosion associated with a nitromethane complexing agent. Still another advantage of the present invention is that the dimethylcarbonate or dimethyloxalate form a 1:1 complex with 18-crown-6, so that only an equimolar amount of the complexing agent must be removed from the separated complex.

Accordingly, the present invention relates to a novel complex formed between 1,4,7,10,13,16-hexaoxacyclooctadecane (18-crown-6) depicted by the structural formula I,

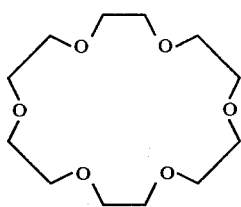

and dimethylcarbonate or dimethyloxalate and to a process for isolating said 18-crown-6 from a mixture containing the compound which comprises:
(a) contacting the mixture with dimethylcarbonate or dimethyloxalate thereby causing the 18-crown-6 to react with the dimethylcarbonate or dimethyloxalate and form, respectively, an 18-crown-6-dimethylcarbonate or an 18-crown-6-dimethyloxalate complex substantially in the form of a dispersed solid in the resulting solution of non-complexed material;
(b) separating the dispersed complex from the resulting solution; and
(c) disassociating the separated complex to afford uncomplexed 18-crown-6.

The process according to the present invention is very effective in that, under optimum conditions, the 18-crown-6 may be isolated with high efficiency and also in high purities exceeding 98% (based on starting amount of 18-crown-6). These excellent results obtain from the fact dimethylcarbonate and dimethyloxalate selectively complex with 18-crown-6, even in the presence of one or more other macrocyclic polyethers. Moreover, 18-crown-6 can be easily obtained from the separated complexes since dimethylcarbonate and dimethyloxalate can be removed quantitatively by keeping the complexes under reduced pressure, e.g., at a pressure between 5 pascal and 6 kilopascal at room temperature or at moderate temperature.

DESCRIPTION OF THE PREFERRED EMBODIMENTS

The novel 18-crown-6-dimethylcarbonate complex according to the present invention can be suitably prepared by treating 18-crown-6, either as such or when present in a mixture, with dimethylcarbonate at a temperature between −30° C. and +30° C., preferably between 0° C. and +20° C. and most preferably between 0° C. and 10° C. The novel 18-crown-6-dimethyloxalate complex according to the present invention can be suitably prepared by treating a mixture comprising 18-crown-6 with dimethyloxalate at temperatures between −30° C. and +40° C., preferably between 0° C. and 30° C. For example, with dimethyloxalate excellent results are obtained at ambient temperature.

The 18-crown-6-complex can be easily separated from the solution containing non-complexed material by any conventional liquid-solid separation technique, for example by filtration, centrifugation or decantation.

While the exact structures have not been fully ascertained, the novel complexes appear to be of the 1:1 type, i.e., one mole of 18-crown-6 per mole of dimethylcarbonate or dimethyloxalate. Accordingly, 18-crown-6 is suitably reacted with the complexing agents using a molar ratio of complexing agent to 18-crown-6 of not less than 1:1. Preferably, this molar ratio is not higher than 10:1, although this range is not critical. An additional advantage inherent with the use of such a 1:1 complex is that only an equimolar amount of the complexing agent has to be removed from the separated complex.

The process according to the present invention is of particular interest in that it affords the selective isolation of 18-crown-6 from mixtures containing this compound, even in the presence of one or more other macrocyclic polyethers such as 1,4,7,10,13-pentaoxacyclopentadecane (15-crown-5).

The process according to the present invention is preferably carried out in an environment which contains a solvent wherein 18-crown-6 is soluble and wherein the solubility of the resulting complex is substantially lower. For purposes of this description, a solvent is taken to consist substantially of a specified compound when the content of this specific compound in the solvent is more than 50% w.

A particularly good class of solvents comprises the class of dialkyl ethers, for instance di-ethylether, di-n-butylether and methyl-t-butylether. Solid complexes are normally formed immediately when using the above-mentioned ethers. Dialkyl diethers, such as dimethoxyethane and diethoxyethane, can also be used advantageously as solvents.

Cyclic ethers such as the dioxanes and tetrahydrofuran can also be used as solvents, preferably in relatively small amounts and at lower temperatures. Dimethylcarbonate itself can also be used as a solvent in the process for the preparation of the 18-crown-6-dimethylcarbonate complex.

The 18-crown-6 complexes may also be formed when alkanols, such as methanol, ethanol, isopropanol or 1,2-dihydroxyethane, are used as solvents. Further solvents comprise ketones such as acetone and methylethylketone as well as hydrocarbons or mixtures of hydrocarbons (e.g., benzene, toluene or the xylenes and aliphatic hydrocarbons such as hexane and heptane). Mixtures of solvents may also be used. When alkanols, ketones or hydrocarbons are used as solvents, it is preferred that the mixtures be maintained at lower temperatures for at least several hours to facilitate formation of the complexes. The use of water alone as a solvent is not recommended, as it appears to prevent complex formation. However, amounts of water up to 25% can be tolerated when using water-miscible solvents.

The 18-crown-6 in the starting mixture may be treated with the complexing agent in any suitable manner, for example by adding the complexing agent to the starting mixture and, if desired, cooling the mixture thus obtained to a temperature at which the complex readily precipitates. Alternatively, the starting mixture may be dissolved in a suitable solvent and the complexing agent, either neat or in the presence of a suitable solvent, added at ambient or somewhat lower temperatures to the solution obtained. As a further alternative, the starting mixture may be treated with a solution of the complexing agent in a suitable solvent. The starting mixture may be solid or liquid at the temperature at which 18-crown-6 is treated with dimethylcarbonate. If the starting mixture is so treated with dimethylcarbonate at a temperature below the melting point (−0.5° C.) of dimethylcarbonate, it is contemplated that the starting mixture will be a liquid at the temperatures used, or alternatively, that a solvent will be used to afford a liquid solution. Since the starting mixture is suitably treated with dimethyloxalate at a temperature below the melting point (54.0° C.) of dimethyloxalate, it is similarly contemplated that the starting mixture will be a liquid at the temperatures used, or alternatively, that a solvent will be used to afford a liquid solution.

As discussed hereinbefore, dimethylcarbonate and dimethyloxalate can selectively isolate 18-crown-6 from mixtures comprising 18-crown-6 whether or not in the presence of one or more other related macrocyclic polyethers. High efficiencies in the recovery of pure 18-crown-6 have been achieved starting from unpurified reaction mixtures containing about 15% w of 18-crown-6 (e.g., as obtained by the catalytic oligomerization of ethylene oxide as in U.S. Pat. No. 3,928,386), as well as from mixtures containing about 50% w of 18-crown-6, even when the remaining 50% w of the mixture consists of the closely related compound 15-crown-5. It is also possible to isolate 18-crown-6 from reaction mixtures wherein an alkali metal halide, e.g., potassium chloride, is also present, either as such or complexed with 18-crown-6. The reaction mixture should then be treated after the complex formation with the complexing agents with a solvent wherein the complex is soluble, e.g., methylene chloride, in order to remove by filtration the alkali metal salt. It is also possible to add the complexing agent and the desired solvent together.

The separated 18-crown-6 complexes according to the present invention can be readily disassociated into 18-crown-6 and the complexing agent by treatment at sub-atmospheric pressure and, if desired, under gentle heating, e.g., to temperatures up to 80° C., followed by removal of the complexing agent. Normally pressures between 5 and 1,000 pascal will be sufficient but lower pressure can also be applied. Alternatively, it is also possible to decompose the 18-crown-6 complexes, especially the 18-crown-6-dimethylcarbonate complex, by heating at atmospheric pressure without distilling 18-crown-6.

The invention will now be illustrated by reference to the following examples, which are not to be construed as limiting its scope. When the amount of complexing agent in the examples is expressed in equivalents, it is intended to denote a molar amount of complexing agent that is a multiple by the number shown of the molar amount of 18-crown-6 present in the solution.

EXAMPLE 1

(a) 18-crown-6-dimethylcarbonate complex

5 Equivalents of dimethylcarbonate were added to a solution of 53 mg 18-crown-6 in 1 ml diethylether at 25° C. A solid complex was formed immediately. The precipitated crystals were filtered off at atmospheric pressure. The crystals contained 81% of the starting amount of 18-crown-6. A melting point range of 39°–54° C. was observed.

The NMR spectrum of the crystals, recorded at 90 MHz in deuterochloroform solution, showed—relative to a tetramethylsilane standard—an absorption at $\delta = 3.688$ ppm, indicating the presence of 18-crown-6, and an absorption at $\delta = 3.792$ ppm, indicating the presence of dimethylcarbonate. The molar ratio of 18-crown-6 to dimethylcarbonate in the 18-crown-6-dimethylcarbonate complex, calculated from the NMR spectrum was 1:1.01 (±0.05). Dimethylcarbonate was removed quantitatively from the complex by maintaining it under reduced pressure (2.6 kilopascal) for 30 minutes at room temperature. A similar experiment was carried out by forming the complex at +4° C. Again a solid complex was formed immediately. The crystals obtained after filtration contained 85% of the starting amount of 18-crown-6.

(b) 18-crown-6-dimethyloxalate complex

2 Equivalents of dimethyloxalate were added to a solution of 53 mg 18-crown-6 in 1 ml of diethylether at 25° C. A solid complex was formed immediately. The precipitated crystals were filtered off at atmospheric pressure and washed with 1 ml of a 0.425 M solution of dimethyloxalate in diethylether. The crystals contained 80% of the starting amount of 18-crown-6. A melting point range of 62°–82° C. was observed.

The NMR spectrum of the crystals, recorded at 90 MHz in deuterochloroform solution, showed—relative to a tetramethylsilane standard—an absorption at $\delta = 3.688$ ppm, indicating the presence of 18-crown-6, and an absorption at $\delta = 3.919$ ppm, indicating the presence of dimethyloxalate. The molar ratio of 18-crown-6 to dimethyloxalate in the 18-crown-6-dimethyloxalate complex, calculated from the NMR spectrum was 1:0.96.

Dimethyloxalate was removed quantitatively from the complex by maintaining it at a pressure of 50 pascal for two hours at 70° C.

EXAMPLE 2

Solid 18-crown-6-dimethylcarbonate complex formation in various solvents

In this series of experiments, solid complexes were formed when dimethylcarbonate (5 equivalents) was added to a solution of 18-crown-6 (0.2 M) in the solvents shown in Table I at the temperatures indicated therein. The recovery (%) of 18-crown-6 from the complex after 24 hours as well as the molar ratios of 18-crown-6 to dimethylcarbonate in the complex (determined by NMR spectroscopy) are also given in Table I. The dimethylcarbonate was removed from the complex in the manner as indicated in Example I.

TABLE I

| Example | Solvent | Recovery of 18-crown-6 (%) from dimethylcarbonate complex after 24 hours at | | Molar Ratio |
|---|---|---|---|---|
| | | 25° C. | 4° C. | |
| 2a | (nC$_4$H$_9$)$_2$O | 85 | 95 | 1:1.10 |
| 2b | CH$_3$O t-C$_4$H$_9$ | 57[1] | 87 | 1:1.01 |
| 2c | (CH$_3$O)$_2$CO | x | 73[1] | 1:0.96 |
| 2d | CH$_3$OCH$_2$CH$_2$OCH$_3$ | x | 49[1] | 1:0.94 |
| 2e | CH$_3$OH | x | 18[1] | 1:0.98 |

TABLE I-continued

| Example | Solvent | Recovery of 18-crown-6 (%) from dimethylcarbonate complex after 24 hours at 25° C. | 4° C. | Molar Ratio |
|---|---|---|---|---|
| 2f | tetrahydrofuran | | 50[2] | 1:1.06 |

[1] solid complex formed over a period of 1-4 hours
[2] solid complex formed when applying higher concentrations
[x] no solid complex formed within 24 hours

EXAMPLE 3

Solid 18-crown-6-dimethyloxalate complex formation in various solvents

In this series of experiments, solid complexes were formed when dimethyloxalate (2 equivalents) was added to a solution of 18-crown-6 (0.2 M) in the solvents shown in Table II at the temperatures indicated therein. The recovery (%) of 18-crown-6 from the complex after 24 hours as well as the molar ratios of 18-crown-6 to dimethyloxalate in the complex (determined by NMR spectroscopy) are also given in Table II. The dimethyloxalate was removed from the complex in the manner as indicated in Example I.

TABLE II

| Example | Solvent | Recovery of 18-crown-6 (%) from dimethylcarbonate complex after 24 hours at 25° C. | 5° C. | −20° C. | Molar Ratio |
|---|---|---|---|---|---|
| 3a | (nC$_4$H$_9$)$_2$O | 71[1] | | | 1:0.97 |
| 3b | CH$_3$O t-C$_4$H$_9$ | 73 | | | 1:0.99 |
| 3c | CH$_3$OCH$_2$CH$_2$OCH$_3$ | x | 52 | | 1:0.99 |
| 3d | CH$_3$OH | x | 49 | | 1:1.00 |
| 3e | tetrahydrofuran | x | x | 59 | 1:1.14 |

[1] experiment carried out at higher dilution (2x) because of limited solubility of dimethyloxalate
[x] no solid complex formed within 24 hours

EXAMPLE 4

Solid 18-crown-6 complex formation in various solvents

In this series of experiments, solid complexes were formed when the indicated complexing agent was added to a solution of 18-crown-6 in the indicated solvent, in a manner similar to that in Examples 2 and 3. The experiments using benzene or 1,4-dioxane as solvents were carried out at higher concentrations (5×). The results are shown in Table III. All experiments were carried out at 25° C.

TABLE III

| Example | Solvent | Complexing Agent* | Recovery of 18-crown-6 (%) from complex | Molar Ratio |
|---|---|---|---|---|
| 4a | n-heptane | A | 52 | 1:0.96 |
| 4b | n-heptane | B | 50 | 1:1.04 |
| 4c | benzene | A | 59 | 1:1.07 |
| 4d | 1,4-dioxane | A | 37 | 1:0.98 |
| 4e | 1,4-dioxane | B | 50 | 1:0.96 |

*A = dimethylcarbonate; B = dimethyloxalate

EXAMPLE 5

Isolation of 18-crown-6 from mixtures using dimethylcarbonate

In this series of experiments, 18-crown-6 was isolated from mixtures containing this compound via the 18-crown-6-dimethylcarbonate complex formed by selective complexation of the 18-crown-6 with dimethylcarbonate at 4° C. the 18-crown-6 containing mixtures were:

A: a crude reaction mixture containing 15% (w/w) 18-crown-6;

B: a reaction mixture containing 50% (w/w) 18-crown-6; and

C: a mixture (1:1) of 15-crown-5 and 18-crown-6.

The purity of the 18-crown-6 obtained after decomposition of the respective complexes in the manner described in Example 1a was in all cases 98%. The solvents employed, the amounts of reaction mixture and dimethylcarbonate used as well as the efficiency of the isolation procedure, i.e. the percentage of 18-crown-6 recovered after decomposition of the complexes, are given in Table IV.

TABLE IV

| Example | Mixture containing 18-crown-6 (g) | Solvent (ml) | Dimethylcarbonate (ml) | Efficiency (%) |
|---|---|---|---|---|
| 5a | A-(3.4) | (C$_2$H$_5$)$_2$O-(5.1) | 1.0 | 82 |
| 5b | A-(3.0) | — | 8.0 | 85 |
| 5c | B-(1.0) | (C$_2$H$_5$)$_2$O-(2.0) | 0.5 | 80 |
| 5d | B-(1.0) | CH$_3$O-tC$_4$H$_9$-(2.0) | 0.5 | 84 |
| 5e | B-(1.0) | — | 2.0 | 80 |
| 5f | C-(0.1) | (C$_2$H$_5$)$_2$O-(1.0) | 0.1 | 83 |

EXAMPLE 6

Isolation of 18-crown-6 from a mixture using dimethyloxalate

A reaction mixture (1 g) containing 50% 18-crown-6 was treated with a solution of dimethyloxalate (0.33 g) in diethylether (3 ml) at room temperature. The precipitated complex was separated by filtration and washed with a solution of dimethyloxalate (0.2 g) in diethylether (2 ml). The yield of the crystals of the 18-crown-6-dimethyloxalate complex obtained was 81%, calculated on the starting amount of 18-crown-6, with the purity of the crystals being in excess of 98%.

EXAMPLE 7

Isolation of 18-crown-6 from mixtures using dimethyloxalate

A series of experiments treating mixtures of 18-crown-6 with dimethyloxalate in diethylether were carried out according to the procedures described in Example 6. The results are given in Table V. Efficiency is again defined as the percentage of 18-crown-6 recovered after decomposition of the complex.

TABLE V

| Mixture containing 18-crown-6 (g) | Solvent (ml) | Dimethyloxalate (g) | Efficiency (%) |
|---|---|---|---|
| A[1] - (2.2) | 5 | 0.5 | 80 |
| C[1] - (0.2) | 2 | 0.2 | 86 |

TABLE V-continued

| Mixture containing 18-crown-6 (g) | Solvent (ml) | Dimethyloxalate (g) | Efficiency (%) |
|---|---|---|---|
| $D^2$ - (5.0) | 10 | 2.2 | 92 |

[1]reaction mixtures defined in Example 5
[2]unpurified reaction mixture containing 16% 18-crown-6 from the synthesis of 18-crown-6 in the manner described in J.C.S. Chem. Commun. (1978) 504.

What is claimed is:

1. The complex between 1,4,7,10,13,16-hexaoxacyclooctadecane (18-crown-6) and dimethylcarbonate or dimethyloxalate containing one molecule of dimethylcarbonate or dimethyloxalate per molecule of 18-crown-6.

2. A process for isolating 18-crown-6 from a mixture containing the compound which comprises:
   (a) contacting the mixture with dimethylcarbonate or dimethyloxalate thereby causing the 18-crown-6 to react with the dimethylcarbonate or dimethyloxalate and form, respectively, an 18-crown-6-dimethylcarbonate or an 18-crown-6-dimethyloxalate complex substantially in the form of a dispersed solid in the resulting solution of non-complexed material;
   (b) separating the dispersed complex from the resulting solution; and
   (c) disassociating the separated complex to afford uncomplexed 18-crown-6.

3. The process according to claim 2, wherein the reaction is carried out in the presence of a solvent for the 18-crown-6.

4. The process according to claim 3, wherein the solvent for the 18-crown-6 substantially consists of an ether, an alkanol or a ketone.

5. The process according to claim 4, wherein the solvent for the 18-crown-6 is a dialkylether.

6. The process according to claim 5, wherein the solvent for the 18-crown-6 is diethylether, di(n-butyl)ether or methyl-t-butyl ether.

7. The process according to claim 2, wherein the complex formation between 18-crown-6 and dimethylcarbonate is carried out at a temperature in the range of from −30° C. to +30° C.

8. The process according to claim 7, wherein the complex formation between 18-crown-6 and dimethylcarbonate is carried out at a temperature in the range from 0° C. to +20° C.

9. The process according to claim 2, wherein the complex formation between 18-crown-6 and dimethyloxalate is carried out at a temperature in the range from −30° C. to +40° C.

10. The process according to claim 9, wherein the complex formation between 18-crown-6 dimethyloxalate is carried out at a temperature in the range from 0° C. to +30° C.

11. The process according to claim 2, wherein the 18-crown-6 is reacted with dimethylcarbonate or dimethyloxalate using a molar ratio of dimethylcarbonate or dimethyloxalate to 18-crown-6 in the range from 1:1 to 10:1.

12. The process according to claim 2, wherein the 18-crown-6 containing mixture contains one or more macrocyclic polyethers.

13. The process according to claim 2, wherein the separated complex is disassociated at sub-atmospheric pressure and a temperature up to about 80° C.

* * * * *